United States Patent [19]

Jizomoto

[11] Patent Number: 4,762,720

[45] Date of Patent: * Aug. 9, 1988

[54] PROCESS FOR PREPARING LIPOSOME COMPOSITIONS

[75] Inventor: Hiroaki Jizomoto, Osaka, Japan

[73] Assignee: Shionogi & Co., Ltd., Osaka, Japan

[ * ] Notice: The portion of the term of this patent subsequent to Jun. 16, 2004 has been disclaimed.

[21] Appl. No.: 777,675

[22] Filed: Sep. 19, 1985

[30] Foreign Application Priority Data

Sep. 21, 1984 [JP] Japan ................................. 59-199011

[51] Int. Cl.$^4$ ..................... A61K 37/22; A01N 25/26; A01N 25/28; B32B 5/16
[52] U.S. Cl. .................................... 424/450; 424/417; 428/402.2; 264/4.1; 264/4.3; 264/4.6
[58] Field of Search ......................... 424/38, 417, 450; 428/402.2; 264/4.1, 4.3, 4.6

[56] References Cited

U.S. PATENT DOCUMENTS 4,310,506  1/1982  Baldeschweiler et al. ...... 428/402.2

*Primary Examiner*—Albert T. Meyers
*Assistant Examiner*—John M. Kilcoyne
*Attorney, Agent, or Firm*—Wenderoth, Lind & Ponack

[57] ABSTRACT

Novel process for liposome compositions capable to retain larger amount of drugs with a small amount of phospholipid and to provide, therefore, safer medications of various drugs, which comprises dispersing freeze-dried MLV or SUV in an aqueous medium in the presence of both an active ingredient and a divalent cation to regenerate LUV or LOV entrapping said active ingredient.

4 Claims, No Drawings

PROCESS FOR PREPARING LIPOSOME COMPOSITIONS

BACKGROUND OF THE INVENTION

1. Field of the Invention

Vesicles, which are so-called "liposomes" consisting of phospholipid bilayers, can be prepared by dispersing a lipid in an aqueous solvent. The liposomes can be useful as a drug-carrier for the administration to subjects if a drug is contained in aqueous compartments in liposome. The present invention relates to processes for preparing liposome compositions containing clinically active ingredients.

2. Prior Art

A process to prepare liposome compositions is disclosed in JPN Unexam. Pat. Pub. No. 53-142514 where the liposome compositions which have been formulated with phospholipid, active ingredient, and adjuvants are freeze-dried for stable storage.

Processes to prepare highly safe liposome compositions are also disclosed in JPN Unexam. Pat. Pub. Nos. 57-82310 and 57-82311 where freeze-dried vesicles are prepared with no organic solvent and are formulated into liposome compositions by the use of an aqueous medium containing any active ingredient.

On the other hand, a process is disclosed in the JPN Unexam. Pat. Pub. No. 58-152812, wherein SUV (small unilamella vesicles) or LUV (large unilamella vesicles) are prepared by dispersing a special phospholipid in an aqueous medium having a specific pH-value.

SUMMARY OF THE INVENTION

A process for preparing liposome compositions which comprises dispersing freeze-dried MLV or SUV in an aqueous medium in the presence of both an active ingredient and a divalent cation to regenerate LUV or LOV (large oligolamella vesicle) entrapping said active ingredient.

DESCRIPTION OF THE PREFERRED EMBODIMENT

A conventional manner for liposome formulation, i.e., hydration method gives only MLV (multilamella vesicles) which is constructed by multiple phospholipid layers and aqueous compartments unless the procedures are carried out under a specific condition, as shown in the JPN Unexam. Pat. Pub. No. 58-152812. When the lyophilizates of these MLV are dispersed in a brine or a buffer which is generally used as an aqueous medium, they are reformed into MLV. In the MLV, the rate of retention of aqueous medium per unit amount of phospholipid is smaller than in the LUV. The captured volume of MLV is, therefore, smaller and the up-take rate of an active ingredient into it is lower.

The present inventor has studied for the purpose of obtaining regenerated LUV or LOV, each of which has a large captured volume and a high uptake-rate of an active ingredient into itself when preparing liposome compositions by dispersing freeze-dried liposomes in an aqueous medium.

The present inventor has found that liposomes can be reformed into LUV or LOV when the lyophilizates of MLV or SUV are dispersed in an aqueous medium if a divalent cation is present in the aqueous medium within a specific range of the concentration. Prior to this invention, the present inventor had found that LUV or LOV is regenerated if the ionic strength of monovalent cation is kept at 0.05 or below in the regeneration procedures (JPN Pat. Appln. No. 59-171265). The fact means that LUV or LOV are never regenerated but MLV if the ionic strength is over 0.05. However in this invention, the presence of a specific amount of a divalent cation prevents the regeneration of MLV and gives desired LUV or LOV.

Lecithins, i.e., saturated or unsaturated phosphatidyl choline, which are lipids composing liposome, are employed for this invention. These lecithins may be combined with phosphatidyl serine, phosphatidyl ethanolamine, phosphatidyl inositol, diphosphatidyl glycolol, phosphatidate, sphingomyelin, or the like; and further with cholesterol or electrically charged substances (e.g., stearylamine, dicetylphosphate). The representatives of them are lecithins derived from yolk, soybean, or tissues of the other animals or plants, hydrogenates thereof, and synthetic lecithins, which may be employed solely or in a mixture of them. For instance, dipalmitoyl phosphatidylcholine, distearoyl phosphatidylcholine, 1-palmitoyl-2-stearoyl phosphatidylcholine, 1-stearoyl-2-palmitoyl phosphatidylcholine, and the like can be employed solely or in combination.

The freeze-dried liposomes employed in this invention are the freeze-dried MLV or SLV prepared by the known method, which may be obtained by means of any method for lyophilization.

Examples of the active ingredients entrapped are anticancer agents such as 5-fluorouracil, neomycin, bleomycin, or the like; antibiotic agents such as chloramphenicol, tetracycline, cefalexin, latamoxef, or the like; enzymes or homologues such as urokinase or the like; peptides such as interferon, interleukin, globulin, insulin or the like; nucleic acids such a DNA, RNA, or the like; vitamins; or the other agents such as sulfamethoxazole, phenobarbital, or the like.

The clinically active ingredients to be entrapped may be ① added to liposome dispersion system just before the freeze-drying or ② dispersed along with freeze-dried liposome: thus obtained mixture is dispersed in an aqueous medium containing a proper divalent cation to regenerate a liposome composition. Alternatively, the active ingredient may be ③ dissolved or dispersed in the aqueous medium in which freeze-dried liposomes have been dispersed, whereby the freeze-dried liposomes are regenerated.

Water, brine (e.g., isotonic saline), buffer (e.g., phosphate buffer, trisaminomethane buffer) or the like is employed as an aqueous medium in which the freeze-dried liposomes are dispersed: the choice depends on the purposes for which the resulting liposome composition is used.

Divalent cation in this invention means metallic ion including calcium, magnesium, zinc, manganese, iron, cobalt, nickel, or the like; particularly, calcium, manganese, or magnesium gives significant effects. When freeze-dried SUV or MLV are dispersed in an aqueous medium containing divalent cation, they are reformed into LUV or LOV: the optimum concentration of the divalent cation varies with the sort of the metallic ion.

There is an optimum range of concentrations on each ion, for instance, the optimum range on calcium is about $3 \times 10^{-3}$ to $1 \times 10^{-1}$M, about $4 \times 10^{-3}$ to $1 \times 10^{-1}$M on magnesium, about $8 \times 10^{-4}$ to $1 \times 10^{-1}$M on manganese: the sort of the metallic ions and their concentrations may be determined by the purpose of using liposome compositions.

When the freeze-dried liposomes prepared from synthetic lecithin are applied to regeneration according to the aforementioned disclosure JPN Pat. Appln. No. 59-171265, liposomes are not regenerated if the procedures are carried out below the gelphase/liquid crystalphase transition temperature of the lecithin used. In order to accomplish this invention on the freeze-dried liposome, it should be noted that the system must be warmed up over said temperature.

Thus obtained liposome compositions may be orally or parenterally administered to subjects directly or in the state of the purified dispersion by removing the excessive active agent remaining outside the liposome by the method of centrifugal separation, ultrafiltration, gelfiltration, or the like.

The present invention is explained in more detail by the following examples, which do not limit the scope of this invention.

EXAMPLE 1

Commercially available yolk lecithin (made by Merck & Co.) was further refined by silica gel chromatography. Chloroform solution of 354 mg of the refined lecithin was placed in a 200 ml round-bottom flask and evaporated to dryness by a rotary evaporator to give a thin layer of the phospholipid on the inner wall of the flask. To the adequately dried layer was added a mixture (30 ml) of water with 1.5 parts of mannitol and the mixture was shaken with hands to prepare a dispersion of MLV. The dispersion was frozen with dry-ice/acetone and freeze-dried by a vacuum pump. 1% Aqueous human serum albumin (HSA) containing sodium chloride (NaCl 0.05M) and/or calcium chloride (CaCl$_2$ 0.03M) was added to the freeze-dried substance at a rate of 0.4 ml to 25 mg of the freeze-dried substance (10 mg as lecithin) at room temperature. The mixture was allowed to stand for an hour while being occasionally shaken, combined with 5 ml of an isotonic aqueous NaCl, and divided by means of ultra-cetrifugal separation (85,000 g×60 minutes) into the external solution and liposomes. The isolated liposomes were dispersed again in another 5 ml of said isotonic NaCl and centrifugally separated. By the quantitative analysis of HSA in the accumulative external solution, the up-take rate of HSA into liposomes on their regeneration were measured (Table 1).

Table 1 shows positive effect of calcium ion to and negative effect of sodium ion against the formation of liposomes having large captured volume.

HSA was quantitatively analyzed according to Lowry's method (Shin Jikken Kagaku-Koza 20-I, 130 published by Maruzen).

TABLE 1

| | Ion | Uptake rate (%) of HSA | Captured Vol.* (μl/mg lipid) |
|---|---|---|---|
| 1 | None | 37.3 | 12.4 |
| 2 | 0.03 M of CaCl$_2$ | 45.1 | 15.5 |
| 3 | 0.05 M of NaCl | 11.6 | 2.1 |
| 4 | 0.03 M CaCl$_2$, 0.05 M NaCl | 34.8 | 11.4 |

*The value of the captured volume is free from HSA (6.2% to uptake rate) adsorbed on the liposome surfaces.

EXAMPLE 2

In the same manner as in Example 1, 262 mg of a hydrogenated yolk lecithin (iodine value 3, Asahi Chem. Ind.) were employed for the formation of the thin layer on the inner wall of a round-bottom flask. Purified water (20 ml) was added thereto to give a dispersion of MLV.

The dispersion was freeze-dried to leave powder. To 10 mg of the freeze-dried powder was added 0.4 ml of aqueous solution of 5-fluorouracil (5-FU, 10 mg/ml) containing NaCl (0.05M) and/or CaCl$_2$ (0.03M), and the mixture was allowed to stand for about an hour then warmed up and kept at 60° C. for 5 minutes. The mixture was allowed to stand at room temperature approximately for another 1 hour and mixed with 5 ml of isotonic aqueous NaCl. Thus obtained liposome dispersion was subjected to centrifugal separation (85,000 g×60 minutes). The precipitated liposomes were collected and dispersed in another 5 ml of isotonic NaCl solution, and isolated again by a centrifugal separator (85,000 g×60 minutes). Finally, thus isolated liposomes were broken by Triton X-100 whereby the released 5-FU was quantitatively analyzed by high performance liquid chromatography (column: Nucleosil 10C$_{18}$, solvent: 0.01M KH$_2$PO$_4$).

TABLE 2

| | Ion | Uptake rate (%) of 5-FU | Captured Vol.* (μl/mg lipid) |
|---|---|---|---|
| 1 | 0.03 M CaCl$_2$ | 31.3 | 12.5 |
| 2 | 0.05 M NaCl | 22.6 | 9.0 |
| 3 | 0.05 M NaCl, 0.03 M CaCl$_2$ | 32.7 | 13.1 |

The results on Table 2 suggest that semi-synthetic phospholipids such as hydrogenated yolk lecithin, when the freeze-dried liposomes composed of them are regenerated, are reformed into liposomes having a large captured volume by the effect of calcium ion like as natural ones (yolk lecithin) or synthetic ones (DPPC).

EXAMPLE 3

In the same manner as in Example 1, MLV was prepared by use of dipalmitoyl phosphatidylcholine (DPPC) and freeze-dried. The freeze-dried MLV (10 mg each) was dispersed in an aqueous solution (0.4 ml) of 19 mM latamoxef containing 0.03M CaCl$_2$ and in that not containing CaCl$_2$. The two mixtures were respectively warmed up and kept at 50° C. for 5 minutes. The uptake rates of latamoxef and the captured volumes of the regenerated liposomes are shown in Table 3.

TABLE 3

| | Ion | Uptake rate (%) of latamoxef | Captured Vol. (μl/mg lipid) |
|---|---|---|---|
| 1 | None | 9.5 | 3.8 |
| 2 | 0.03 M CaCl$_2$ | 36.5 | 14.6 |

EXAMPLE 4

The freeze-dried MLV (10 mg each) composed of DPPC prepared in Example 3 was added to 0.4 ml each of 0.25% aqueous solution of 5-FU containing either one of the salts listed in Tables 4 to 7, and warmed up and kept at 50° C. for 5 minutes. The uptake rates of 5-FU and the captured volumes of the regenerated liposomes are shown in Tables 4 to 7.

TABLE 4

| | Monovalent cation | Divalent metallic ion CaCl$_2$ | Uptake rate (%) | Captured Vol. (μl/mg lipid) |
|---|---|---|---|---|
| 1 | 0.05 M NaCl | None | 4.7 | 1.9 |
| 2 | 0.05 M NaCl | 0.01 M | 40.2 | 16.1 |

TABLE 4-continued

| | Monovalent cation | Divalent metallic ion CaCl$_2$ | Uptake rate (%) | Captured Vol. (μl/mg lipid) |
|---|---|---|---|---|
| 3 | 0.05 M NaCl | 0.05 M | 38.2 | 15.3 |
| 4 | 0.05 M CH$_3$COONa | None | 3.2 | 1.3 |
| 5 | 0.05 M CH$_3$COONa | 0.05 M | 40.5 | 16.2 |
| 6 | 0.05 M CH$_3$COONH$_4$ | None | 3.2 | 1.3 |
| 7 | 0.05 M CH$_3$COONH$_4$ | 0.05 M | 27.2 | 10.9 |

TABLE 5

| | Monovalent cation | Divalent metallic ion | Uptake rate (%) | Captured Vol. (μl/mg lipid) |
|---|---|---|---|---|
| 1 | 0.05 M NaCl | None | 4.7 | 1.9 |
| 2 | 0.05 M NaCl | 0.01 M MgCl$_2$ | 41.5 | 16.6 |
| 3 | 0.05 M NaCl | 0.01 M MnCl$_2$ | 40.7 | 16.3 |
| 4 | 0.05 M NaCl | 0.05 M CoCl$_2$ | 22.0 | 8.8 |
| 5 | 0.05 M NaCl | 0.05 M ZnSo$_4$ | 27.7 | 11.1 |

TABLE 6

| | Concentration of CaCl$_2$ | Uptake rate (%) | Captured Volume (μl/mg lipid) |
|---|---|---|---|
| 1 | 1.0 M | 0.7 | 0.03 |
| 2 | 3.0 mM | 45.9 | 18.4 |
| 3 | 0.5 mM | 3.0 | 1.2 |
| 4 | 0.1 mM | 43.9 | 17.6 |

TABLE 7

| | Concentration of MnCl$_2$ | Uptake rate (%) | Captured Volume (μl/mg lipid) |
|---|---|---|---|
| 1 | 0.2 M | 11.0 | 4.4 |
| 2 | 5.0 mM | 43.2 | 17.3 |
| 3 | 0.5 mM | 4.8 | 1.9 |
| 4 | 0.2 mM | 43.0 | 17.2 |

EFFECTS

The liposome compositions prepared by the present invention have a high uptake-rate and therefore entrap the aimed active ingredient therein in high efficiency. Since each regenerated liposome has a large captured volume, a large amount of the active ingredient is entrapped in it by a less amount of the phospholipid: this means that the liposome compositions keep such troubles away as toxicity accompanied by phospholipid when administered, or the like.

Additionally, both liposome and active ingredients can be stored in a stable state, because the active ingredient to be entrapped may be admixed at the time when the freeze-dried liposomes are regenerated.

What is claimed is:

1. A process for preparing liposome compositions which comprises dispersing freeze-dried multilamella vesicles or small unilamella vesicles prepared from a lecithin in an aqueous medium containing both an active ingredient and a divalent cation selected from the group consisting of calcium, magnesium, zinc, manganese, iron, cobalt, and nickel, the amount of the divalent cation being sufficient to prevent the regeneration of multilamella vesicles and the process being carried out at or above the temperature of the gel-phase/liquid crystal-phase transition temperature of the lecithin employed.

2. A process according to claim 1 in which the divalent cation is selected from the group consisting of calcium in an amount of $3 \times 10^{-3}$M to $1 \times 10^{-1}$M, magnesium in an amount of $4 \times 10^{-3}$M to $1 \times 10^{-1}$M and manganese in an amount of $8 \times 10^{-4}$M to $1 \times 10^{-1}$M.

3. A process according to claim 2 in which the aqueous medium is selected from the group consisting of water, brine, a phosphate buffer and a trisaminomethane buffer.

4. A process according to claim 1 in which the active ingredient is selected from the group consisting of chloramphenicol, tetracycline, cefalexin, latamoxef, urokinase, interferon, interleukin, globulin, insulin, DNA, RNA, vitamins, sulfamethoxazole and phenobarbital.

* * * * *